United States Patent [19]
Gross

[11] Patent Number: 5,911,578
[45] Date of Patent: Jun. 15, 1999

[54] HEAD ASSEMBLY FOR A MEDICAL HANDPIECE

[76] Inventor: Joseph Garyson Gross, 12 Hummingbird Ct., Lake Wylie, S.C. 29710

[21] Appl. No.: 09/103,406

[22] Filed: Jun. 24, 1998

[51] Int. Cl.⁶ ..................................................... A61C 1/14
[52] U.S. Cl. .......................... 433/127; 279/51; 279/125; 433/129
[58] Field of Search .................................. 279/43.2, 463, 279/51, 53, 58, 125; 433/127, 128, 129

[56] References Cited

U.S. PATENT DOCUMENTS

| | | |
|---|---|---|
| 3,499,223 | 3/1970 | Lieb et al. . |
| 3,960,039 | 6/1976 | Nash et al. . |
| 4,015,335 | 4/1977 | Nash . |
| 4,015,489 | 4/1977 | Lieb et al. . |
| 4,493,645 | 1/1985 | Nakanishi .................. 433/127 |
| 4,536,157 | 8/1985 | Maizenberg .............. 433/129 |
| 5,040,980 | 8/1991 | Heil . |
| 5,542,846 | 8/1996 | Quinn . |

*Primary Examiner*—Daniel W. Howell
*Assistant Examiner*—Monica Smith
*Attorney, Agent, or Firm*—Adams Law Firm, P.A.

[57] ABSTRACT

A head assembly for a medical handpiece includes a head housing and a rotor spindle contained in the housing. The spindle defines a longitudinal through-bore with an internal screw thread. An adjustable chuck is received within the through-bore of the spindle and has a complementary external screw thread adapted for mating with the internal thread of the spindle. The chuck has a top opening forming a keyway and a bottom opening adapted for receiving and holding a bur. A chuck key is attached to the housing, and includes a hand grip at its top end for being manipulated by a user and a chuck engaging bottom end. The chuck key is axially moveable between an operative position and an inoperative position. Upon rotation of the chuck key in the operative position, the chuck threadably moves relative to the spindle to an open position for receiving and removing the bur. Upon counter-rotation of the chuck key in the operative position, the chuck threadably moves relative to the spindle to a closed position for adjustably tightening around the bur. Upon rotation of the chuck key in the inoperative position, the chuck is immovable.

14 Claims, 4 Drawing Sheets

HEAD ASSEMBLY FOR A MEDICAL HANDPIECE

TECHNICAL FIELD AND BACKGROUND OF THE INVENTION

This invention relates to a head assembly for a medical handpiece, and particularly to a high-speed dental handpiece including a threaded, or Jacob's style, chuck. The chuck carries a dental bur in the head assembly of the handpiece, and is adjustable between an open position for releasing the bur from the handpiece and closed position for attaching the bur to the handpiece. The invention includes means for quickly and conveniently opening and closing the chuck, and for adjustably tightening the attachment of the bur to the handpiece without the use of special tools or equipment.

Prior art chucks commonly used in dental handpieces generally fall into two main categories: those including a screw thread adjustment for tightening and loosening the jaws of the chuck, and those which use a spring for closing the chuck and a release mechanism engaging the spring to open the chuck. Both types of prior art chucks suffer from drawbacks and limitations.

The conventional threaded chuck requires a separate chuck tool for engaging and adjusting the chuck. The tool is generally difficult to handle, must be separately sterilized, and must be readily available for chair-side use. If the tool is lost or misplaced, the handpiece is essentially useless. The spring type chuck offers the convenience of a release mechanism incorporated directly within the head of the handpiece, but fails to provide means for adjustably tightening the grip of the chuck on the bur. The unreliability of the attachment of the bur to the handpiece can result in poor dental work and possible injury to the patient. Moreover, spring type chucks are generally applicable only for certain dental burs, and do not allow for bur shaft diameter variations. Other disadvantages of these prior art chucks are discussed in prior U.S. Pat. Nos. 5,542,846 and 5,040,980. The disclosures of these patents are incorporated herein by reference.

SUMMARY OF THE INVENTION

Therefore, it is an object of the invention to provide a head assembly for a dental handpiece which combines the convenience of an integral chucking mechanism and the ability to adjustably tighten the attachment of the bur to the handpiece.

It is another object of the invention to provide a head assembly for a dental handpiece which uses a threaded, or Jacob's style, chuck.

It is another object of the invention to provide a head assembly for a dental handpiece which does not require a separate tool for opening and closing the chuck.

It is another object of the invention to provide a head assembly for a dental handpiece which has a relatively low profile, about 1.5 cm, for allowing the head assembly to be comfortably inserted into the mouth of the patient.

It is another object of the invention to provide a head assembly for a dental handpiece which allows convenient chair-side tightening and loosening of the bur.

It is another object of the invention to provide a head assembly for a dental handpiece which avoids inadvertent loosening of the bur during operation of handpiece.

It is another object of the invention to provide a head assembly for a dental handpiece which includes means for quickly releasing the bur from the handpiece.

It is another object of the invention to provide a head assembly for a dental handpiece which allows quick and convenient parts replacement without substantial disassembly or delay.

These and other objects of the present invention are achieved in the preferred embodiments disclosed below by providing a head assembly for a medical handpiece, and a handpiece incorporating a head assembly of the present invention. The head assembly includes a head housing and a rotor spindle contained in the housing. The spindle defines a longitudinal through-bore with an internal screw thread. An adjustable chuck is received within the through-bore of the spindle and has a complementary external screw thread adapted for mating with the internal thread of the spindle. The chuck has a top opening forming a keyway and a bottom opening adapted for receiving and holding a bur. A chuck key is attached to the housing, and includes a hand grip at its top end for being manipulated by a user and a chuck-engaging bottom end. The chuck key is axially moveable between an operative position wherein its bottom end is received within the keyway of the chuck, and an inoperative position wherein its bottom end is axially spaced from the keyway of the chuck. Upon rotation of the chuck key in the operative position, the chuck threadably moves relative to the spindle to an open position for receiving and removing the bur. Upon counter-rotation of the chuck key in the operative position, the chuck threadably moves relative to the spindle to a closed position for adjustably tightening around the bur. Upon rotation of the chuck key in the inoperative position, the chuck is immovable.

According to one preferred embodiment of the invention, a back cap is removably attached to a back of the housing and includes an interior wall defining a cap opening in axial alignment with the through-bore of the rotor spindle for receiving the bottom end of the chuck key into the housing.

According to another preferred embodiment of the invention, the back cap includes an open top, a cylindrical side wall, and an annular retaining flange spaced-apart from the interior wall. The side wall, interior wall, and flange cooperate to form a cap housing.

According to yet another preferred embodiment of the invention, a floating spacer disk is positioned in the cap housing and includes a disk opening in axial alignment with the cap opening and the through-bore of the spindle for receiving the bottom end of the chuck key into the housing.

According to yet another preferred embodiment of the invention, biasing means are located between the interior wall of the back cap and the spacer disk for normally urging the spacer disk upwardly against the annular flange of the back cap. The chuck key is normally urged into the inoperative position axially spaced from the chuck.

According to yet another preferred embodiment of the invention, a locking cylinder has an enlarged top received within a complementary-shaped recess adjacent the opening of the spacer disk, and a body portion for being received within the cap opening of the back cap. The locking cylinder has an opening in axial alignment with the through-bore of the spindle for receiving the bottom end of the chuck key into the housing.

According to yet another preferred embodiment of the invention, the locking cylinder includes at least one downward projecting finger adapted for extending into at least one notch formed adjacent the through-bore of the rotor spindle upon axial movement of the chuck key into the operative position. The finger holds the spindle stationary upon rotation and counter-rotation of the chuck relative to the spindle.

BRIEF DESCRIPTION OF THE DRAWINGS

Some of the objects of the invention have been set forth above. Other objects and advantages of the invention will appear as the description proceeds when taken in conjunction with the following drawings, in which.

DESCRIPTION OF THE PREFERRED EMBODIMENT AND BEST MODE

Figure 1:
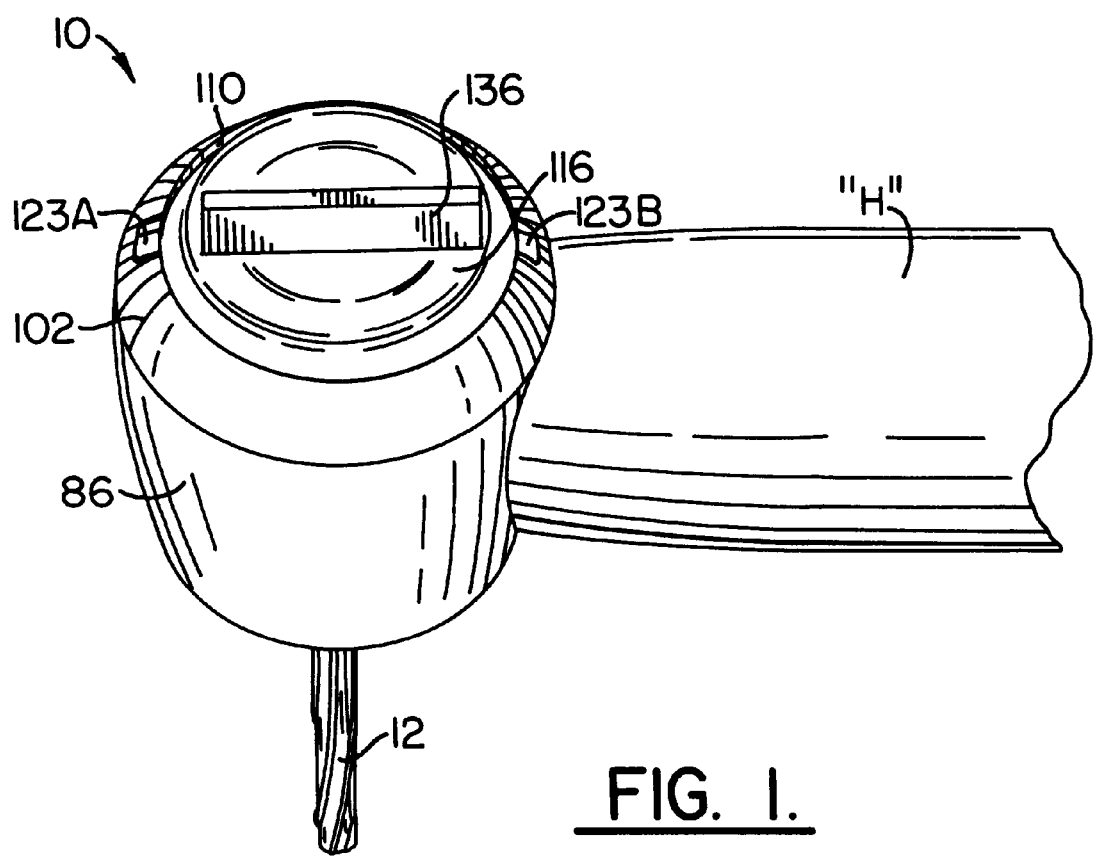
FIG. 1 is a fragmentary perspective view of a dental handpiece including a head assembly according to one preferred embodiment of the present invention.

Referring now specifically to the drawings, a head assembly for a dental handpiece "H" according to the present invention is illustrated in FIG. 1 and shown generally at reference numeral 10. The handpiece "H" carries a replaceable, rotating dental bur 12 used for cutting, grinding, and polishing the teeth of a patient. The bur 12 is adjustably attached to the head assembly 10 of the handpiece "H", and is quickly and conveniently released from the handpiece "H" without the use of a separate tool.

Figure 2:
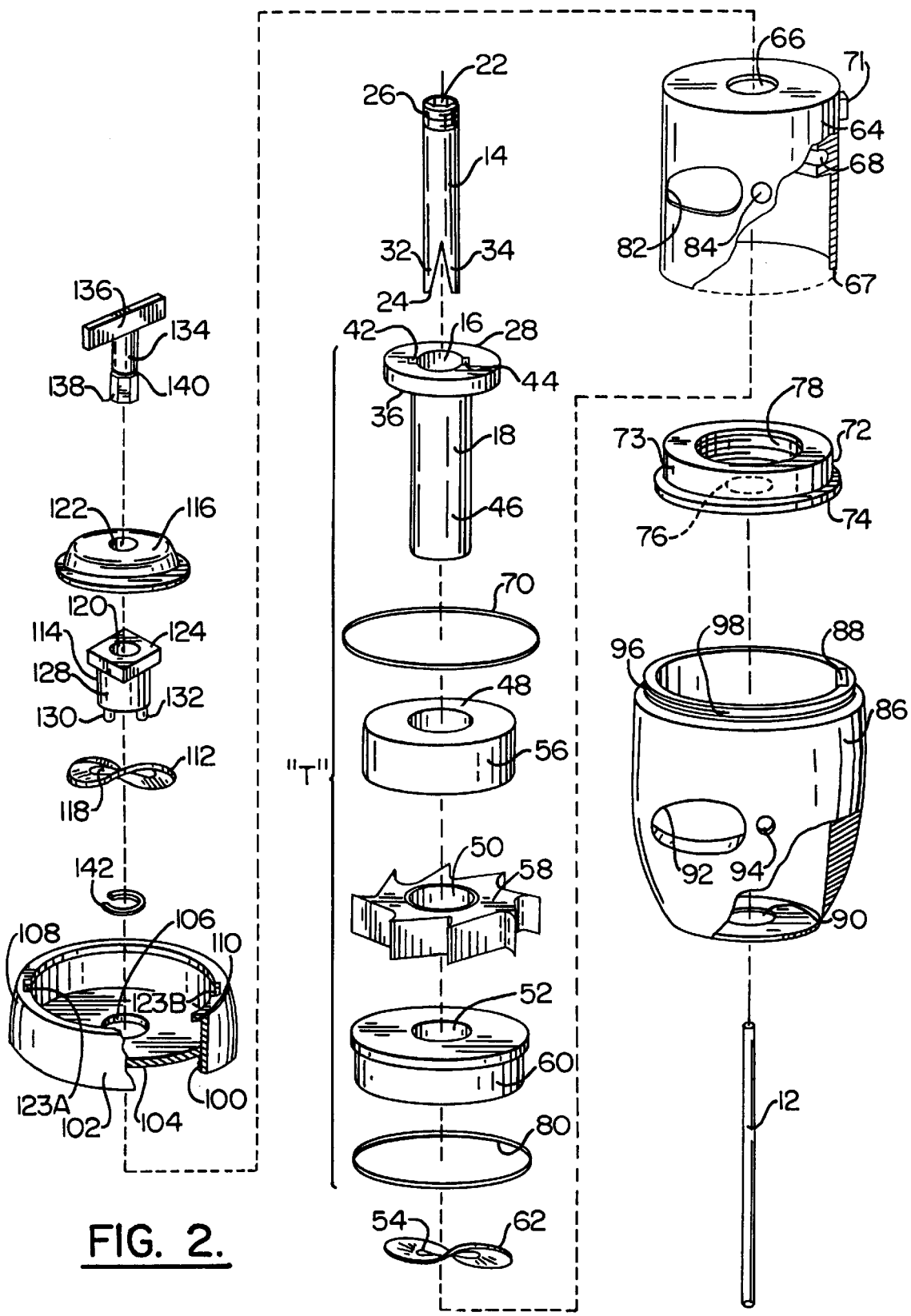
FIG. 2 is an exploded view of the head assembly of the handpiece with portions of the head housing, canister, and back cap broken away.

As best shown in FIG. 2, the head assembly 10 includes a chuck 14, such as a Jacob's chuck, received within the longitudinal through-bore 16 of a rotor spindle 18, and having a top opening 22 defining a hex-shaped keyway and a bottom opening 24 adapted for receiving and holding the bur 12. The top end of the chuck 14 includes an external screw thread 26 which mates with a complementary internal thread 28 of the spindle 18 to secure the chuck 14 inside the spindle 18. A pair of spring jaws 32 and 34 formed at the bottom end of the chuck 14 cooperate to enlarge and constrict the bottom opening 24 upon threadably advancing and retracting the chuck 14. The through-bore 16 of the spindle 18 preferably tapers inwardly towards the bottom end of the spindle 18 such that when the chuck 14 is advanced in the direction of the taper, the opening 24 closes around the bur 12. When the chuck 14 is retracted in a direction away from the taper, the opening 24 enlarges to allow removal and insertion of the bur 12.

Figure 3:
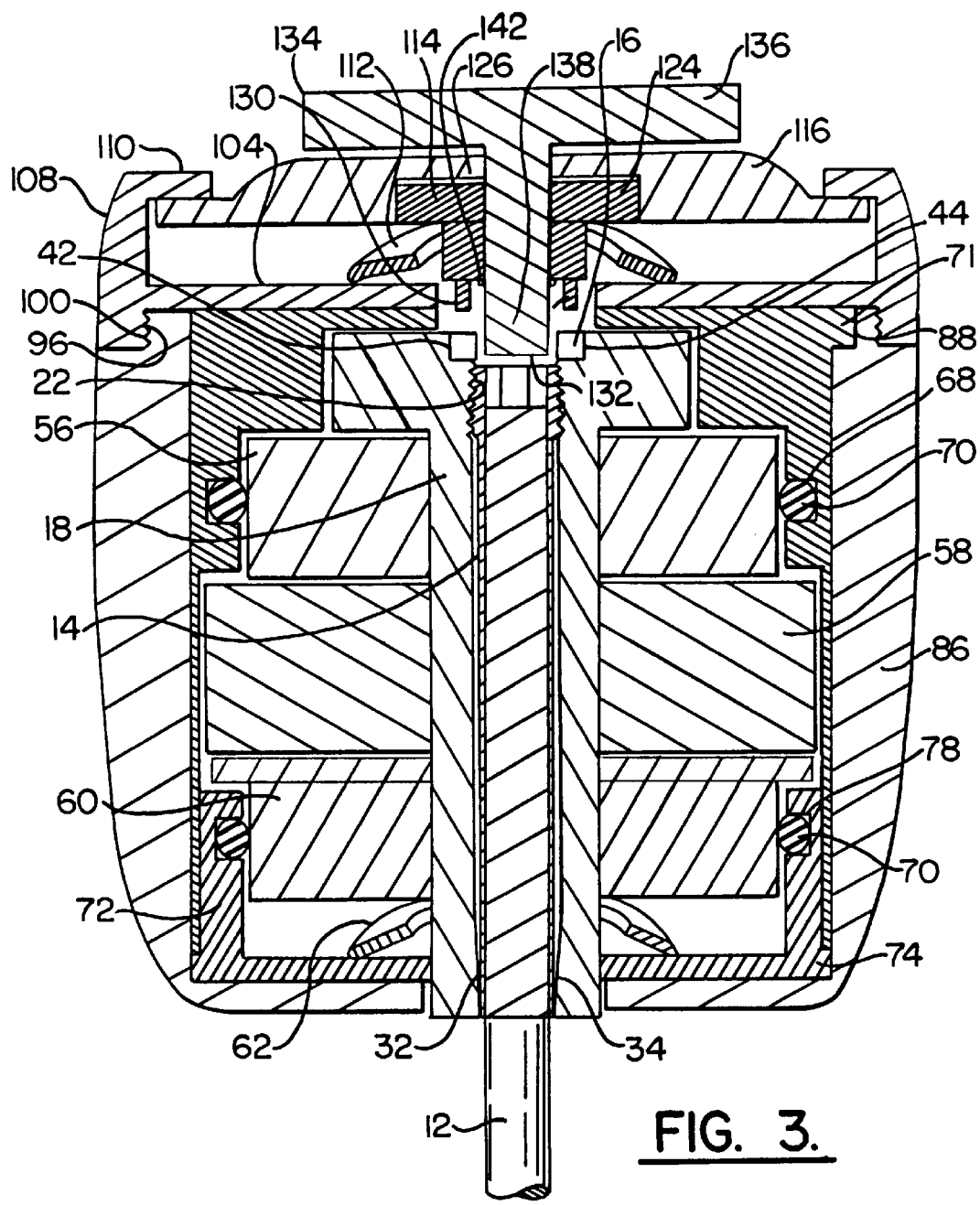
FIG. 3 is a cross-sectional view of the head assembly of the handpiece with the chuck key in the inoperative position.
Figure 4:
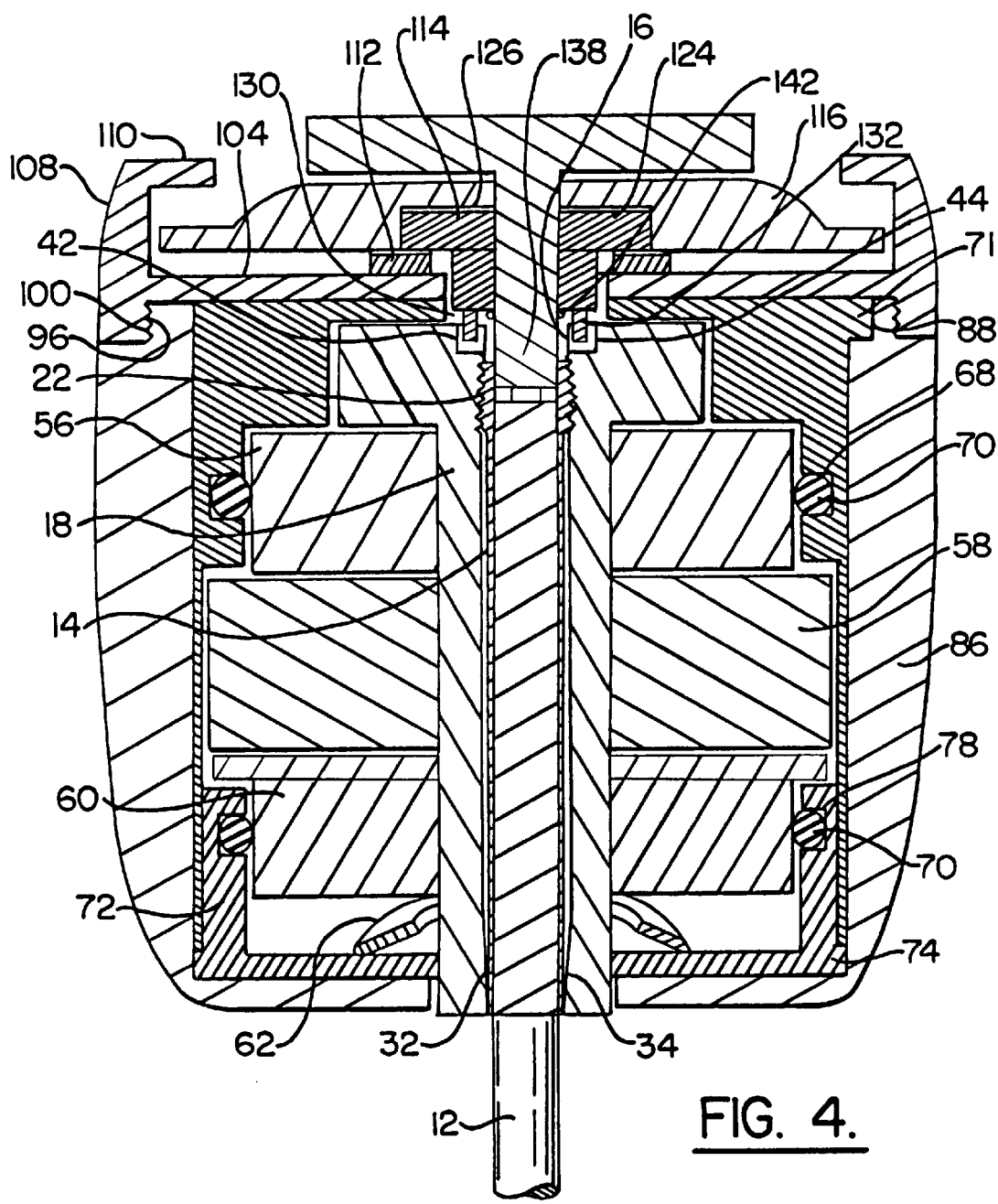
FIG. 4 is a cross-sectional view of the head assembly of the handpiece with the chuck key in the operative position.

The spindle 18 includes an enlarged annular top flange 36 with opposing notches 42 and 44 formed adjacent the through-bore 16, and a cylindrical body portion 46 adapted for extending through axially-aligned openings 48, 50, 52, and 54 in a rear bearing 56, impeller 58, flange bearing 60, and spring washer 62. The spindle 18, rear bearing 56, impeller 58, and flange bearing 60 collectively form a turbine assembly "T" which cooperates with forced air through the handpiece "H" to effect high-speed rotation of the bur 12. The turbine assembly "T" fits within a canister 64, as shown in FIGS. 3 and 4.

The canister 64 has a top center opening 66 for being aligned with the through-bore 16 of the spindle 18, an open bottom 67, an interior groove 68 for holding an O-ring 70, and an alignment peg 71. A removable bottom cover 72 with a cylindrical portion 73 is received through the open bottom 67 of the canister 64, and includes an annular flange 74 which sits adjacent the bottom edge of the canister 64 when assembled. The bottom cover 72 further includes a center opening 76 for receiving the bottom end of the spindle 18, and an interior groove 78 for holding a second O-ring 80.

Respective air intake and exhaust openings 82 and 84 are formed in a side wall of the canister 64 between the O-rings 70 and 80 for receiving and exhausting forced air used to actuate the impeller 58, and thereby operate the handpiece "H". The O-rings 70 and 80 cooperate to stabilize the turbine assembly "T" and create a pneumatic seal on opposite sides of the impeller 58. The operational details of the handpiece "H" and turbine assembly "T" are well known and understood in the art.

Upon assembly of the interior components, as described above, the bottom cover 72 is positioned over the open bottom 67 of the canister 64 and the canister 64 placed inside a head housing 86. The alignment peg 71 is received in a notch 88 to ensure proper alignment of the air intake and exhaust openings 82 and 84 of the canister 64. The spring washer 62 maintains proper spacing of the turbine assembly "T" inside the canister 64. Should the turbine assembly "T" require servicing, the entire canister 64 is conveniently removed from the housing 86 and replaced with a new canister 64 and turbine assembly "T" without substantial disassembly or delay.

The head housing 86 includes a bottom opening 90 for inserting and removing the bur 12, and air intake and exhaust openings 92 and 94 aligned with the intake and exhaust openings 82 and 84 of the canister 64. The top of the housing 86 defines a reduced diameter connecting portion 96 with an external screw thread 98 adapted for mating with a complementary internal thread 100 of a back cap 102.

The back cap 102 has a recessed interior wall 104 with an opening 106 which aligns with the through-bore 16 of the spindle 18 upon assembly of the back cap 102 and head housing 86. The back cap 102 further includes a cylindrical side wall 108 and an annular retaining flange 110 which cooperate with the interior wall 104 to form a cap housing. A spring washer 112, locking cylinder 114, and floating spacer disk 116 are arranged in the cap housing and have respective openings 118, 120, and 122 formed in axial alignment with the cap opening 106. The spacer disk 116 is preferably slightly larger in diameter than the open top of the cap housing and is normally urged against the retaining flange 110 of the back cap 102 by the spring washer 112, as shown in FIG. 3. Preferably, the retaining flange 110 has a pair of spaced notches 123A and 123B, shown in FIGS. 1 and 2, for receiving prongs of a tool for removing and attaching the back cap 102.

The locking cylinder 114 includes an enlarged square top 124 located in a complementary-shaped bottom recess 126 (See FIGS. 3 and 4) formed adjacent the opening 122 of the spacer disk 116, and a body portion 128 with projecting fingers 130 and 132. The body portion 128 of the cylinder 114 is received through the opening 118 of the spring washer 112, and is adapted for extending through the cap opening 106 to position the fingers 130 and 132 within the notches 42 and 44 formed in the spindle 18.

A chuck key 134 is received through the openings 122 and 120 of the spacer disk 116 and locking cylinder 114, and includes a hand grip 136 for being manipulated by the user and a hex end 138 for being inserted into the keyway 22 of the chuck 14. Preferably, the key 134 has a groove 140 above the hex end 138 for holding a retaining ring 142 to prevent removal of the key 134 through the cylinder opening 120.

Operation of the chuck key 134 is illustrated in FIGS. 3 and 4. FIG. 3 shows the head assembly 10 of the handpiece "H" with the key 134 in an inoperative position. Spring washer 112 engages the locking cylinder 114, as described above, and forces the spacer disk 116 away from the interior wall 104 of the back cap 102. The annular periphery of the spacer disk 116 is urged against the retaining flange 110. The key 134 is freely rotatable in this position without effecting the attachment of the bur 12 to the head assembly 10 of the handpiece "H".

In order to open or close the chuck 14, the user depresses the spacer disk 116 and key 134 against the biasing force of the spring washer 112 and manually rotates the key 134 until the fingers 130 and 132 of the locking cylinder 114 enter the notches 42 and 44 of the spindle 18 and the hex end 138 of the key 134 enters the hex-shaped keyway 22 of the chuck 14. Slight friction between the key 134 and locking cylinder 114 is sufficient to rotate the locking cylinder 114 upon rotation of the key 134.

With the key 134 in the operative position, as shown in FIG. 4, the user further rotates the key 134 in a clockwise or counterclockwise direction to threadably advance or retract the chuck 14 within the spindle 18. The enlarged square top 124 of the locking cylinder 114 received within the square-shaped bottom recess 126 of the spacer disk 116 holds the spacer disk 116 and locking cylinder 114 stationary as the key 134 rotates. Threadably retracting the chuck 14 within the spindle 18 in a direction away from the tapered end of the through-bore 16 causes the spring jaws 32 and 34 to open, thereby loosening their grip on the bur 12 so that the bur 12 can be repositioned in the chuck 14, or removed and replaced. Threadably advancing the chuck 14 in the spindle 18 towards the tapered end of the through-bore 16 causes the spring jaws 32 and 34 to close together, thereby strengthening their grip on the bur 12. The strength of the grip on the bur 12 is adjustable, as desired, depending on how far the chuck 14 is advanced within the spindle 18.

A head assembly for a dental handpiece is described above. Various details of the invention may be changed without departing from its scope. Furthermore, the foregoing description of the preferred embodiment of the invention and the best mode for practicing the invention are provided for the purpose of illustration only and not for the purpose of limitation—the invention being defined by the claims.

I claim:

1. A head assembly for a medical handpiece, comprising:
    (a) a head housing;
    (b) a rotor spindle contained in said housing and defining a longitudinal through-bore with an internal screw thread;
    (c) an adjustable chuck received within the through-bore of said rotor spindle and having a complementary external screw thread adapted for mating with the internal thread of said spindle, said chuck having a top opening forming a keyway and a bottom opening adapted for receiving and holding a bur; and
    (d) a chuck key attached to said housing, and including a hand grip at a top end thereof for being manipulated by a user and a chuck-engaging bottom end, said chuck key being axially moveable between an operative position wherein its bottom end is received within the keyway of said chuck, and an inoperative position wherein its bottom end is axially spaced from the keyway of said chuck, such that:
        (i) upon rotation of said chuck key in the operative position, said chuck threadably moves relative to said spindle to an open position for receiving and removing the bur, and upon counter-rotation of said chuck key in the operative position, said chuck threadably moves relative to said spindle to a closed position for adjustably tightening around the bur; and
        (ii) upon rotation of said chuck key in the inoperative position, said chuck is immovable.

2. A head assembly according to claim 1, and comprising a back cap removably attached to a back of said housing and including an interior wall defining a cap opening therein in axial alignment with the through-bore of said rotor spindle for receiving the bottom end of said chuck key into said housing.

3. A head assembly according to claim 2, wherein said back cap includes an open top, a cylindrical side wall, and an annular retaining flange spaced-apart from the interior wall, said side wall, interior wall, and flange cooperating to form a cap housing.

4. A head assembly according to claim 3, and comprising a floating spacer disk positioned in the cap housing and including a disk opening therein in axial alignment with said cap opening and the through-bore of said spindle for receiving the bottom end of said chuck key into said housing.

5. A head assembly according to claim 4, and comprising biasing means located between the interior wall of said back cap and said spacer disk for normally urging said spacer disk upwardly against the annular flange of said back cap, whereby said chuck key is normally urged into the inoperative position axially spaced from said chuck.

6. A head assembly according to claim 5, and comprising a locking cylinder having an enlarged top received within a complementary-shaped recess adjacent the opening of said spacer disk, and a body portion for being received within the cap opening of said back cap, said locking cylinder having an opening in axial alignment with the through-bore of said spindle for receiving the bottom end of said chuck key into said housing.

7. A head assembly according to claim 6, wherein said locking cylinder includes a downward projecting finger adapted for extending into a notch formed adjacent the through-bore of said rotor spindle upon axial movement of said chuck key into the operative position, such that said finger holds said spindle stationary upon rotation and counter-rotation of said chuck relative to said spindle.

8. In combination with a medical handpiece, a head assembly comprising:
    (a) a head housing;
    (a) a rotor spindle contained in said housing and defining a longitudinal through-bore with an internal screw thread;
    (b) an adjustable chuck received within the through-bore said rotor spindle and having a complementary external thread adapted for mating with the internal thread of said spindle, said chuck having a top opening forming a keyway and a bottom opening adapted for receiving and holding a bur; and
    (c) a chuck key attached to said housing, and including a hand grip at a top end thereof for being manipulated by a user and a chuck-engaging bottom end, said chuck key being axially moveable between an operative position wherein its bottom end is received within the keyway of said chuck, and an inoperative position wherein its bottom end is axially spaced from the keyway of said chuck, such that:
        (i) upon rotation of said chuck key in the operative position, said chuck threadably moves relative to said spindle to an open position for receiving and removing the bur; and upon counter-rotation of said chuck key in the operative position, said chuck threadably moves relative to said spindle to a closed position for adjustably tightening around the bur; and (ii) upon rotation of said chuck key in the inoperative position, said chuck is immovable.

9. A combination according to claim 8, and comprising a back cap removably attached to a back of said housing and including an interior wall defining a cap opening therein in axial alignment with the through-bore of said rotor spindle for receiving the bottom end of said chuck key into said housing.

10. A combination according to claim 9, wherein said back cap includes an open top, a cylindrical side wall, and an annular retaining flange spaced-apart from the interior wall, said side wall, interior wall, and flange cooperating to form a cap housing.

11. A combination according to claim 10, and comprising a floating spacer disk positioned in the cap housing and including a disk opening therein in axial alignment with said cap opening and the through-bore of said spindle for receiving the bottom end of said chuck key into said housing.

12. A combination according to claim 11, and comprising biasing means located between the interior wall of said back cap and said spacer disk for normally urging said spacer disk upwardly against the annular flange of said back cap, whereby said chuck key is normally urged into the inoperative position axially spaced from said chuck.

13. A combination according to claim 12, and comprising a locking cylinder having an enlarged top received within a complementary-shaped recess formed adjacent the opening of said spacer disk, and a body portion for being received within the cap opening of said back cap, said locking cylinder having a cylinder opening in axial alignment with the through-bore of said spindle for receiving the bottom end of said chuck key into said housing.

14. A combination according to claim 13, wherein said locking cylinder includes a downward projecting finger adapted for extending into a notch formed adjacent the through-bore of said rotor spindle upon axial movement of said chuck key into the operative position, such that said finger holds said spindle stationary upon rotation and counter-rotation of said chuck relative to said spindle.

* * * * *